(12) United States Patent
Serna

(10) Patent No.: US 10,639,073 B1
(45) Date of Patent: May 5, 2020

(54) EXFOLIATING MAT

(71) Applicant: Kristina Serna, Arcadia, CA (US)

(72) Inventor: Kristina Serna, Arcadia, CA (US)

( * ) Notice: Subject to any disclaimer, the term of this patent is extended or adjusted under 35 U.S.C. 154(b) by 283 days.

(21) Appl. No.: 15/703,537

(22) Filed: Sep. 13, 2017

Related U.S. Application Data

(60) Provisional application No. 62/393,868, filed on Sep. 13, 2016.

(51) Int. Cl.
*A61B 17/54* (2006.01)
*A47K 3/00* (2006.01)
*A47K 7/02* (2006.01)
*A61B 17/32* (2006.01)

(52) U.S. Cl.
CPC .............. *A61B 17/54* (2013.01); *A47K 3/002* (2013.01); *A47K 7/026* (2013.01); *A61B 17/320068* (2013.01); *A61B 2017/320008* (2013.01)

(58) Field of Classification Search
CPC ....... A47K 3/002; A47K 7/026; A47L 23/266; A61B 17/54; A61B 17/320068; A61B 2017/320008; A61B 2017/00761
See application file for complete search history.

(56) References Cited

U.S. PATENT DOCUMENTS

| D263,975 | S | * | 4/1982 | Quiroga | 273/274 |
| 5,164,164 | A | * | 11/1992 | Strickler | A47L 23/266 |
| | | | | | 15/104.92 |
| 5,729,858 | A | * | 3/1998 | Riffel | A46B 9/02 |
| | | | | | 15/111 |
| 6,289,528 | B1 | * | 9/2001 | Ridder | A47K 3/002 |
| | | | | | 4/581 |
| 6,662,398 | B1 | * | 12/2003 | Thomson | A47K 7/026 |
| | | | | | 15/104.92 |
| 6,920,655 | B2 | | 7/2005 | Mitchell | |
| 7,451,513 | B2 | * | 11/2008 | Torres | A47K 7/024 |
| | | | | | 15/21.1 |
| 7,578,021 | B1 | | 8/2009 | Figueroa | |
| D623,975 | S | | 9/2010 | Woods | |
| 8,272,799 | B1 | * | 9/2012 | Yard | A46B 13/008 |
| | | | | | 15/21.1 |
| 8,287,976 | B2 | | 10/2012 | Hupp | |
| 8,505,551 | B2 | | 8/2013 | Moretti | |
| 8,545,516 | B1 | * | 10/2013 | Winnett | A61B 17/54 |
| | | | | | 606/131 |
| 2005/0235411 | A1 | * | 10/2005 | Lev | A47K 3/022 |
| | | | | | 4/622 |

(Continued)

OTHER PUBLICATIONS

Avon Wellness Shower Therapy for Feet 4 in 1 Shower / Bath Mat with Pumice Stone, Soap Dispenser. Product listing [online]. © 1996-2018, Amazon.com, Inc. [Retrieved on Jul. 13, 2016]. <URL:https://www.amazon.com/Avon-Wellness-Shower-Therapy-Dispenser/dp/B009CF5342/187-1839162-0105221?ie=UTF&&*Version*=1&*entries*=0>.

(Continued)

*Primary Examiner* — Alexander J Orkin
(74) *Attorney, Agent, or Firm* — Cramer Patent & Design, PLLC; Aaron R. Cramer

(57) ABSTRACT

An exfoliating mat has a first side with a perimeter of silicone gel defining an interior area and a second side having an attachment means adjacent each interior corner of the mat. The interior area of the first side further comprises regions of high grit pumice and low grit sandpaper bound within artistic shapes. An electrical vibrating mechanism is secured within the mat subjacent the low grit regions.

12 Claims, 4 Drawing Sheets

(56) References Cited

U.S. PATENT DOCUMENTS

| | | | |
|---|---|---|---|
| 2007/0089758 A1 | 4/2007 | Koutscumbos | |
| 2012/0042460 A1* | 2/2012 | Kessler | A47L 23/22 |
| | | | 15/97.2 |
| 2014/0222026 A1* | 8/2014 | Tenenbaum | A61B 18/203 |
| | | | 606/131 |
| 2014/0375434 A1* | 12/2014 | Puljan | F21V 33/004 |
| | | | 340/12.5 |
| 2015/0096597 A1* | 4/2015 | Patel | A47L 23/266 |
| | | | 134/18 |

OTHER PUBLICATIONS

Bathroom Non Slip Mat. Product listing [online]. Copyright © 1995-2018 eBay Inc. [Retrieved on Jul. 13, 2016]. <URL: https://www.ebay.com/itm/PVC-Non-Slip-Shower-Mat-Bath-Tub-Mat-Bathroom-Floor-Mat-with-Suction-Cups-Safety-/141819437885?var=&hash=item210518e33d:m:mHEwsmRszxITQSzZzjQYPuw>.

* cited by examiner

EXFOLIATING MAT

RELATED APPLICATIONS

The present invention was first described in and claims the benefit of U.S. Provisional Patent Application No. 62/393,868 filed on Sep. 13, 2016, the entire disclosures of which are incorporated herein by reference.

FIELD OF THE INVENTION

The present invention relates generally to the field of bathroom textiles and more specifically relates to a bathmat system.

BACKGROUND OF THE INVENTION

A bathmat is a device generally on the floor of a bathroom to provide a non-slip surface, and to absorb small amounts of water, similar to a towel, or as a device placed within a shower enclosure or bathtub to increase traction and comfort.

The two (2) basic types of bathmats include the kind placed inside the bathtub/shower to improve traction and therefore safety, as well as the kind that is placed just outside the bathtub for a user to stand and stop upon while exiting the bath/shower. The first type is used to prevent slipping in the tub or provide a softness to a user's feet, while the second type absorbs water from the body after the bath or shower and helps prevent slipping as well as water damage to the floor. Bathmats may be constructed from woven materials, or may be constructed from synthetics or rubberized materials, dependent upon the specific application.

During or shortly after the showering/bathing process, some individuals may prefer to remove excess skin from his/her feet to improve appearance or comfort, often requiring a scouring device, such as a pumice stone or similar device. Such exfoliation of the feet often requires additional effort, increasing the overall time spent during bathing or showering. Also, a separate and generally exclusive exfoliating device is required. A suitable solution is desired.

Various attempts have been made to solve problems found in bathroom textile art. Among these are found in: U.S. Pat. Nos. and U.S. Pat. App. Pub. Nos. 6,530,096, 2008/0235892, and 6,142,156. These prior art references are representative of bathroom textiles.

None of the above inventions and patents, taken either singly or in combination, is seen to describe the invention as claimed. Thus, a need exists for a reliable pumice-lined bathmat, and to avoid the above-mentioned problems.

SUMMARY OF THE INVENTION

In view of the foregoing disadvantages inherent in the prior art, it has been observed that there is need of a reliable pumice-lined bathmat.

To achieve the above and other objectives, the present invention provides for a mat, comprising a top layer, a bottom layer which is secured beneath the top layer defining an inner space therebetween, a border which is secured about a peripheral edge of the top layer, a power source compartment which is secured to a common first border edge and a first bottom layer edge, a power source which is removably secured within the power source compartment, at least one (1) switch which is disposed upon the top layer in electrical communication with the power source, at plurality of vibration mechanisms which disposed is within the inner space in electrical communication with the least one (1) switch and a first grit surface which is disposed upon the top layer. Actuation of the least one (1) switch vibrates the top layer. In a separate embodiment, the bottom layer is removable.

The top layer may comprise a first top layer section, a second top layer section and a middle top layer section which is disposed between the first top layer section and the second top layer section. The middle top layer may comprise a first switch and a second switch adjacent the first switch. The first switch and the second switch may be in electrical communication between the power source and the plurality of vibration mechanisms. The first switch activates the vibration mechanisms while the second switch deactivates the vibration mechanisms.

The first switch may be secured beneath a first design and the second switch may be secured beneath a second design. The first top layer section may comprise a second grit, the middle top layer section may comprise a third grit and the second top layer section may comprise the second grit. The first design may be first footprint and the second design may be a second footprint.

The first top layer section may comprise a third design and the second top layer section may comprise a fourth design. The third design and fourth design may each be a floral motif. An exterior face of the bottom layer may comprise a plurality of suction cups.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
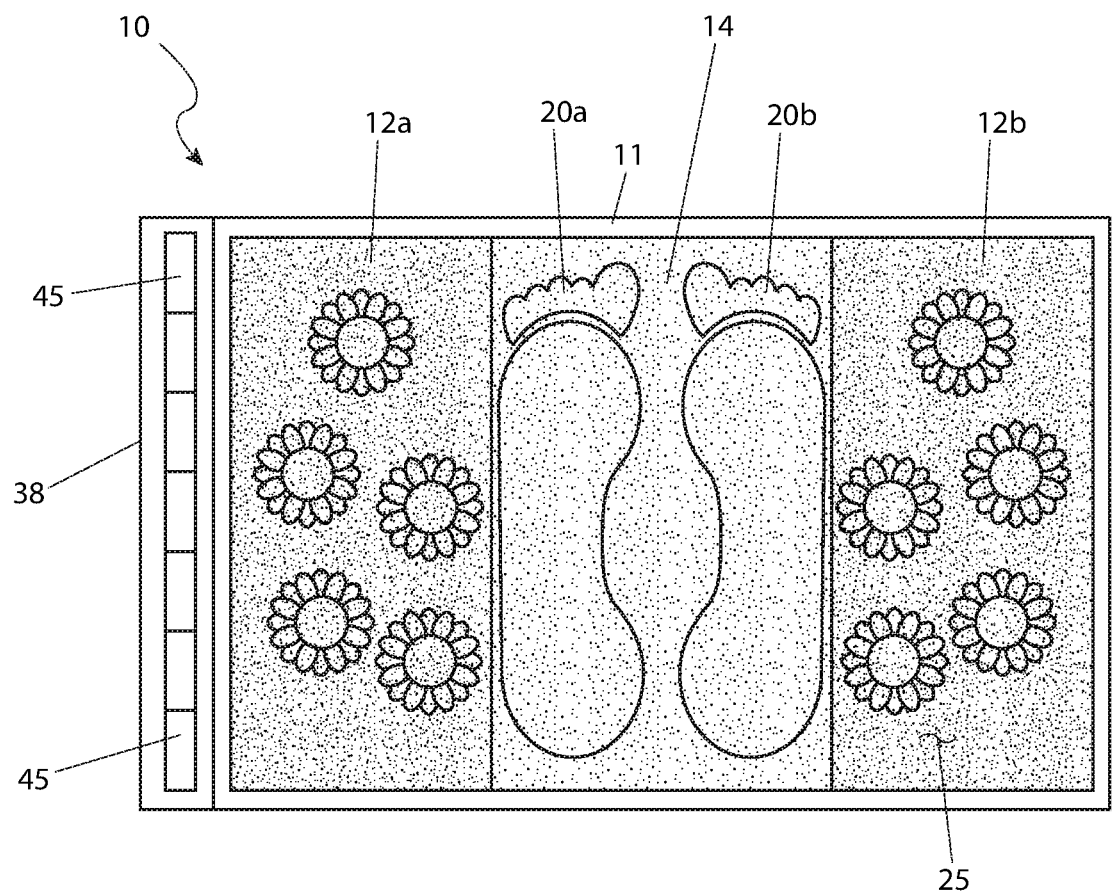
FIG. 1 is a top plan view of a mat 10, according to a preferred embodiment of the present invention.

DESCRIPTIVE KEY 10 mat
11 border
12a first outer section
12b second outer section
14 center section
20a first actuator
20b second actuator
25 top layer
26 bottom layer
30 suction cup
35 battery compartment
40 vibrating apparatuses
45 batteries

DETAILED DESCRIPTION OF THE PREFERRED EMBODIMENT

The best mode for carrying out the invention is presented in terms of its preferred embodiment, herein depicted within FIGS. 1 through 4. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope.

The terms "a" and "an" herein do not denote a limitation of quantity, but rather denote the presence of at least one (1) of the referenced items.

The present invention advantageously fills the aforementioned deficiencies by providing a pumice-lined mat 10 to exfoliate the feet of a user after bathing. The mat 10 is superior to other systems in that it effectively provides a waterproof vibrating mechanism (not shown) to remove excess skin from a user's feet contained within the mat 10 itself, saving time and effort of the user.

Referring now to the drawings, there is shown in FIG. 1 a pumice-lined mat 10. The mat 10 comprises a top layer 25, with a border 11, bonded to a bottom layer 26, and a battery compartment 35. A series of vibrating apparatuses 40 (not visible due to illustrative limitations) is in electrical communication with batteries 45 retained within the battery compartment 35. As shown, the mat 10 may include an external layer of pumice configured to remove rough and/or dead skin from the feet of a user affixable upon a top layer 25. The user may remove the skin from the feet by rubbing his/her feet upon the top layer 25 of the mat 10.

In some embodiments, the mat 10 may include a center section 14 including an external layer of pumice having a first grit. The center section 14 may also have indicia resembling a pair of "footprints". The "toe" sections of the indicia may include a first actuator 20a and a second actuator 20b, each in electrical communication with and capable of activating the respective vibrating apparatuses 40 (not shown in this figure). Adjacent to each side of the center section 14 is a first outer section 12a and a second outer section 12b. These outer sections 12a, 12b further preferably have indicia resembling or including a floral design, or a plurality of flowers, in some embodiments. The outer sections 12a, 12b may additionally include a surface with a second grit. It is preferred that the first grit of the center section 14 has a coarse grit and the second grit of the outer sections 12a, 12b has a grit that resembles emery boards to additionally facilitate the removal of skin from the feet of the user.

The vibrating mechanism is preferably operably connected to the center section 14 but may in alternate embodiments be operably attached to the outer sections 12a 12b as well.

The top of the bottom layer 26 of the mat 10 may be removably affixed to the bottom of the top layer 25 by any suitable means (e.g., hook-and-loop fasteners, buttons, snaps, adhesive, adhesive tape, etc.). The mat 10 may be waterproof in some embodiments, and may be constructed from materials which include organic textiles or silicone-based products.

Figure 2:
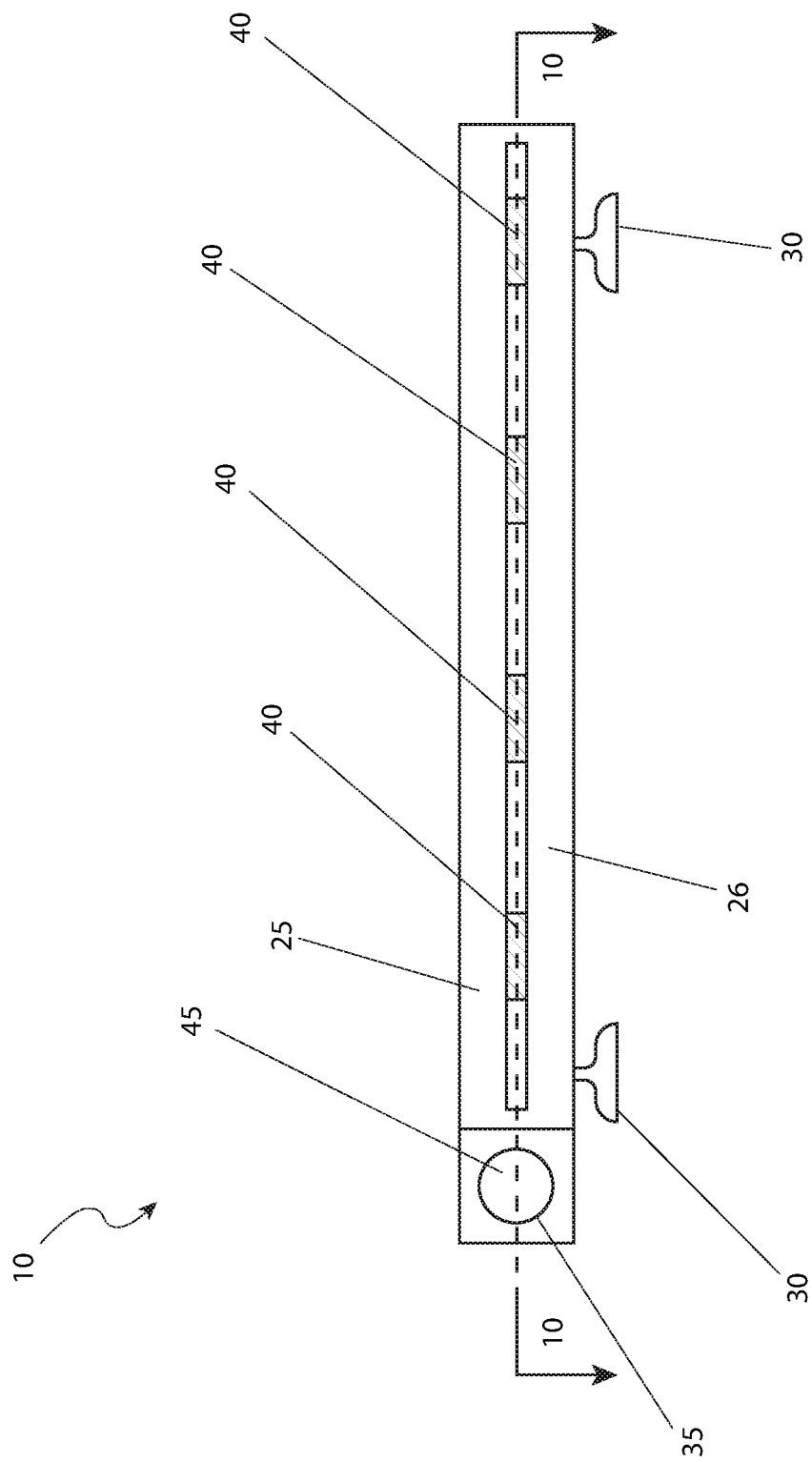
FIG. 2 is a side view of the mat 10, according to a preferred embodiment of the present invention.
Figure 3:
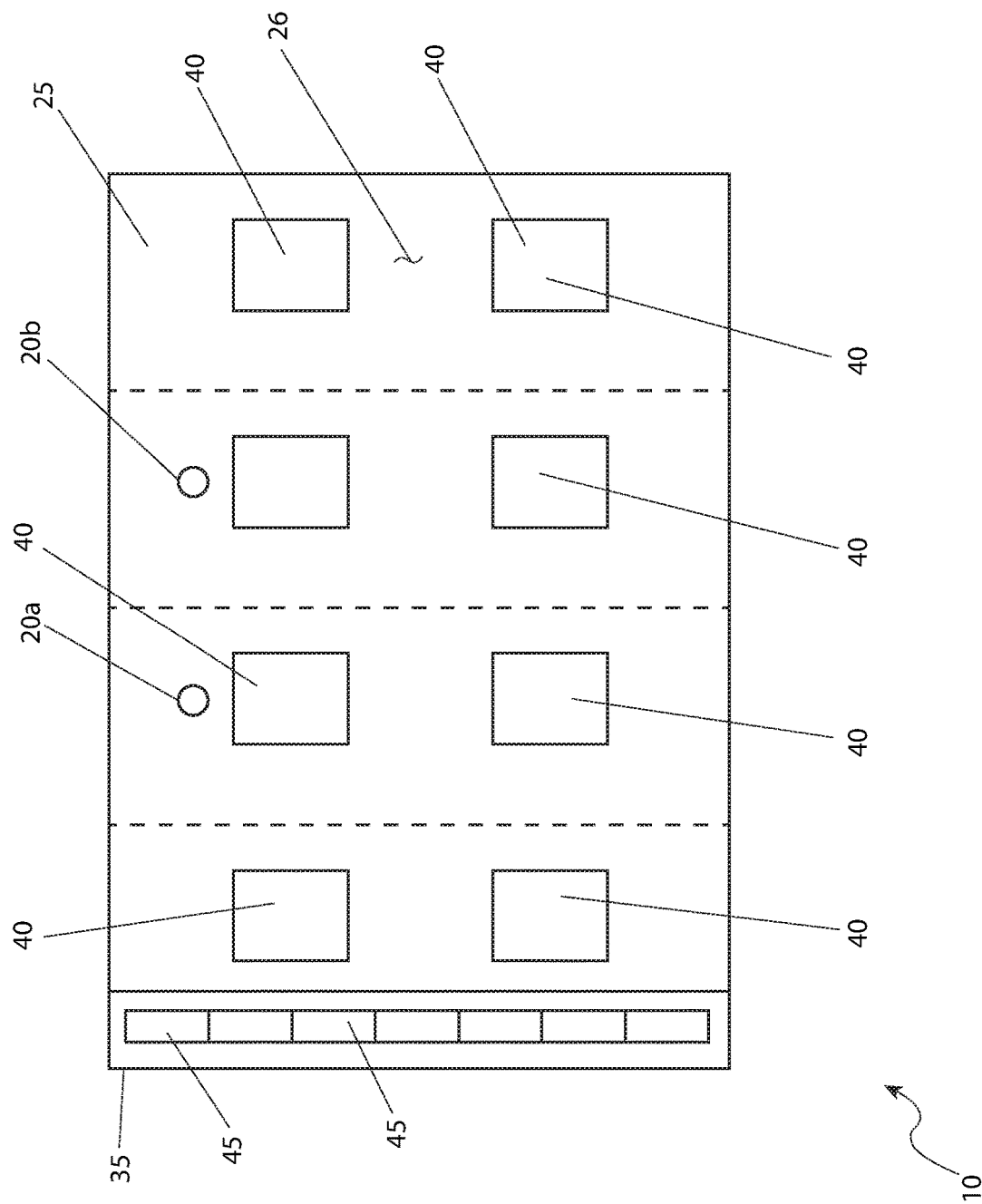
FIG. 3 is a sectional view of the mat 10, as seen along a line I-I, as shown in FIG. 2, according to the preferred embodiment of the present invention; and, FIG. 4 is an electronic schematic diagram of the mat 10, depicting the major electrical components, according to the preferred embodiment of the present invention.

Referring now to FIG. 2, a side view of the mat 10, and FIG. 3, a sectional view of the mat 10, as seen along a line I-I, as shown in FIG. 2, according to the preferred embodiment of the present invention is disclosed. This figure discloses the battery compartment 35 and the batteries 45 contained therein. The top layer 25 and the bottom layer 26 are positioned above and below the vibrating apparatuses 40 respectively. The vibrating apparatuses 40 can be comprised of a wide variety of electrical/mechanical apparatuses including but not limited to motors, motors with offset weights, electromagnet coils, buzzer mechanisms with breaking contacts, or the like. As such, the inclusion or exclusion of any particular type of vibrating device is not intended to be a limiting factor of the present invention. In some embodiments, the bottom of the bottom layer 26 may be removably affixed to a surface, such a bath floor, shower floor, or bathroom floor by any suitable means such as suction cups 30 for providing greater traction, safety, and stability between the mat 10 and the surface to which the mat 10 is placed.

Figure 4:
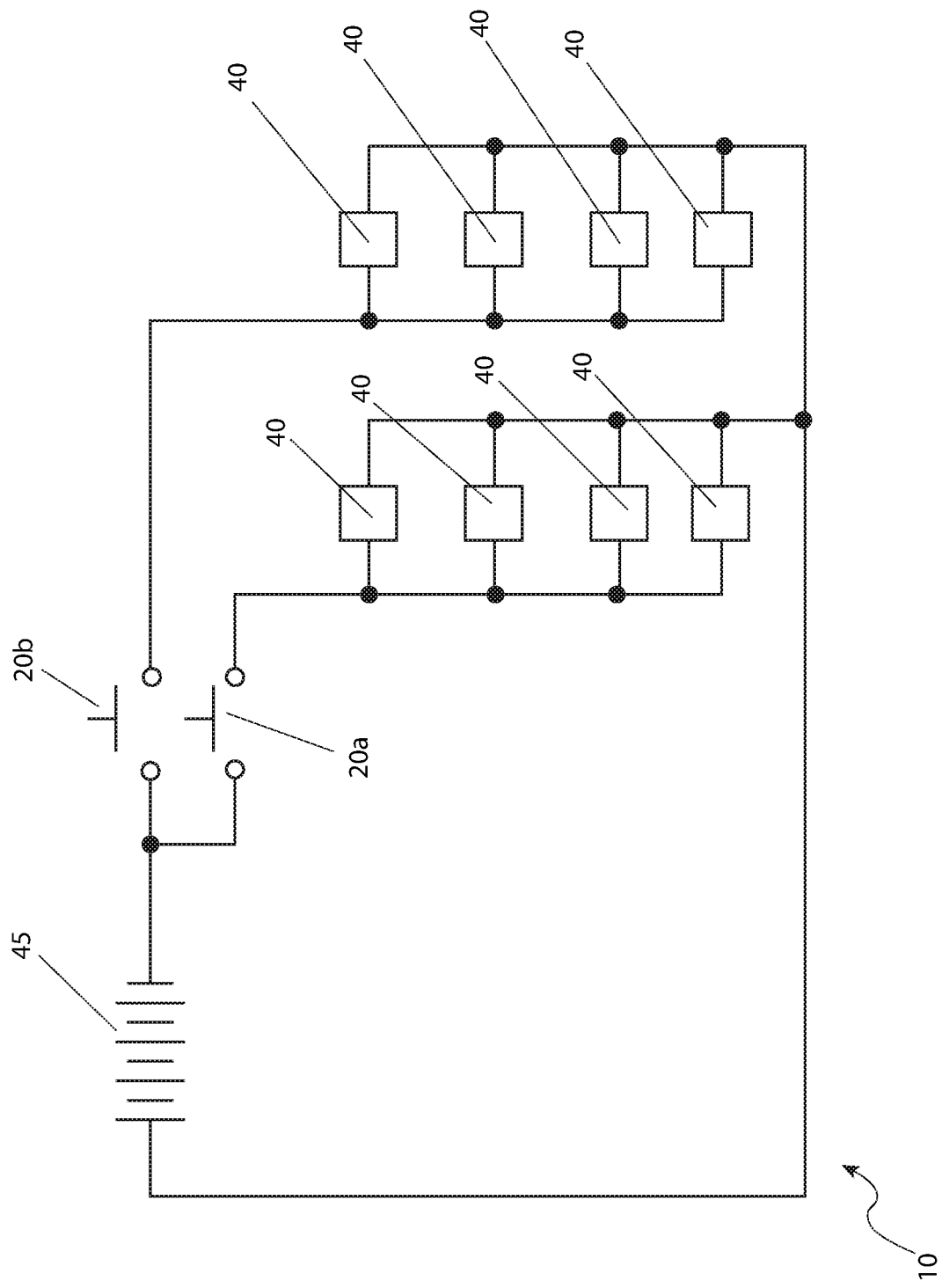

Referring finally to FIG. 4, an electronic schematic diagram of the mat 10, depicting the major electrical components, according to the preferred embodiment of the present invention. Power from the batteries 45 is routed through the first actuator 20a and the second actuator 20b, herein disclosed as momentary action pushbutton-style switches. These devices are arranged in a parallel manner to allow one (1), the other, or both the first actuator 20a and the second actuator 20b, to be actuated at the same time. Output power is then routed to the vibrating mechanisms 40 in a series circuit manner Finally, the plurality of vibrating apparatuses 40 are connected in a parallel manner to allow for energization based upon status of the first actuator 20a and the second actuator 20b. This feature allows the user to actuate the vibration feature of the mat 10 to aid in removal of dead and/or unwanted skin on their feet.

The foregoing descriptions of specific embodiments of the present invention have been presented for purposes of illustration and description. They are not intended to be exhaustive or to limit the invention and method of use to the precise forms disclosed. Obviously, many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

The invention claimed is:

1. An exfoliating mat, comprising:
   a generally rectangular-shaped top layer comprising pumice for exfoliating skin;
   a generally rectangular-shaped bottom layer secured beneath said top layer defining a waterproof inner space therebetween;
   a border secured about a peripheral edge of said top layer;
   a power source compartment secured to a common first border edge and a first bottom layer edge;
   a power source removably secured within said power source compartment;
   at least one switch disposed upon said top layer in electrical communication with said power source;
   a plurality of vibration mechanisms disposed within said inner space in electrical communication with said least one switch; and,
   a first grit surface disposed upon said top layer;
   wherein actuation of said least one switch vibrates said top layer;

wherein said top layer comprises:
  a first top layer section;
  a second top layer section; and,
  a middle top layer section disposed between said first top layer section and said second top layer section; and
wherein said middle top layer comprises:
  a first switch; and,
  a second switch adjacent said first switch;
wherein said first switch and said second switch are in electrical communication between said power source and said vibration mechanisms;
wherein activation of said first switch activates said vibration mechanisms;
wherein activation of said second switch deactivates said vibration mechanisms;
wherein said first switch is secured beneath a first design and said second switch is secured beneath a second design;
wherein said first top layer section comprises a second grit, said middle top layer section comprises a third grit and said second top layer section comprises said second grit; and
wherein an exterior face of said bottom layer comprises a plurality of suction cups.

2. The mat of claim 1, wherein said first design is a first footprint and said second design is a second footprint.

3. The mat of claim 1, wherein said a first top layer section comprises a third design and said second top layer section comprises a fourth design.

4. The mat of claim 3, wherein said third design is a floral motif.

5. The mat of claim 3, wherein said fourth design is a floral motif.

6. An exfoliating mat, comprising:
  a generally rectangular-shaped top layer comprising pumice for exfoliating skin;
  a generally rectangular-shaped bottom layer removably secured beneath said top layer defining a waterproof inner space therebetween;
  a border secured about a peripheral edge of said top layer;
  a power source compartment secured to a common first border edge and a first bottom layer edge;
  a power source removably secured within said power source compartment;
  at least one switch disposed upon said top layer in electrical communication with said power source;
  a plurality of vibration mechanisms disposed within said inner space in electrical communication with said least one switch; and,
  a first grit surface disposed upon said top layer;
wherein actuation of said least one switch vibrates said top layer;
wherein said top layer comprises:
  a first top layer section;
  a second top layer section; and,
  a middle top layer section disposed between said first top layer section and said second top layer section; and
wherein said middle top layer comprising:
  a first switch; and,
  a second switch adjacent said first switch;
wherein said first switch and said second switch are in electrical communication between said power source and said plurality of vibration mechanisms;
wherein activation of said first switch activates said vibration mechanisms; and,
wherein activation of said second switch deactivates said vibration mechanisms; and
wherein an exterior face of said bottom layer comprises a plurality of suction cups.

7. The mat of claim 6, wherein said first switch is secured beneath a first design and said second switch is secured beneath a second design.

8. The mat of claim 7, wherein said first design is a first footprint and said second design is a second footprint.

9. The mat of claim 7, wherein said a first top layer section comprises a third design and said second top layer section comprises a fourth design.

10. The mat of claim 9, wherein said third design is a floral motif.

11. The mat of claim 9, wherein said fourth design is a floral motif.

12. The mat of claim 6, wherein said first top layer section comprises a second grit, said middle top layer section comprises a third grit and said second top layer section comprises said second grit.

\* \* \* \* \*